US009816968B2

(12) United States Patent
Little

(10) Patent No.: US 9,816,968 B2
(45) Date of Patent: Nov. 14, 2017

(54) ANALYSIS OF REAL TIME BACKSCATTER DATA FOR FAULT SIGNAL GENERATION IN A MEDICAL HIFU DEVICE

(75) Inventor: Blake Little, Bothell, WA (US)

(73) Assignee: LIPOSONIX, INC., Bothell, WA (US)

( * ) Notice: Subject to any disclaimer, the term of this patent is extended or adjusted under 35 U.S.C. 154(b) by 1048 days.

(21) Appl. No.: 12/729,447

(22) Filed: Mar. 23, 2010

(65) Prior Publication Data

US 2010/0241034 A1  Sep. 23, 2010

Related U.S. Application Data

(60) Provisional application No. 61/162,641, filed on Mar. 23, 2009.

(51) Int. Cl.
| | | |
|---|---|---|
| *A61H 1/00* | (2006.01) | |
| *G01N 29/30* | (2006.01) | |
| *A61N 7/02* | (2006.01) | |
| *G01N 29/34* | (2006.01) | |
| *G01N 29/44* | (2006.01) | |

(Continued)

(52) U.S. Cl.
CPC .............. *G01N 29/30* (2013.01); *A61N 7/02* (2013.01); *G01N 29/343* (2013.01); *G01N 29/4427* (2013.01); *G01N 29/4454* (2013.01); *A61B 2017/00119* (2013.01); *A61B 2017/00123* (2013.01); *A61B 2017/00725* (2013.01); *A61N 2007/0078* (2013.01); *G01N 2291/044* (2013.01)

(58) Field of Classification Search
CPC ........................................ A61N 7/00
USPC ............................................ 601/2
See application file for complete search history.

(56) References Cited

U.S. PATENT DOCUMENTS 4,122,725 A * 10/1978 Thompson ...................... 73/632
4,647,913 A 3/1987 Pantus
(Continued)

FOREIGN PATENT DOCUMENTS

| DE | 196 25 667 A1 | 1/1998 |
|---|---|---|
| EP | 0 713 102 A1 | 5/1996 |

(Continued)

OTHER PUBLICATIONS

The International Bureau of WIPO, International Preliminary Report on Patentability issued in related International application No. PCT/US2010/028254 dated Sep. 27, 2011.

(Continued)

*Primary Examiner* — Tse Chen
*Assistant Examiner* — Hien Nguyen
(74) *Attorney, Agent, or Firm* — Thompson Hine LLP

(57) ABSTRACT

A method and system for checking functionality of an ultrasound therapy head. The waveform profile for typical ultrasound reflections for a functional therapy head are stored, and before use of a therapy head, an ultrasound energy burst (700) is sent, and the actual waveform profile of the returned reflections (702) are compared to the stored waveform profiles (706). If the actual profiles are not sufficiently close to the stored profiles, then a first signal (712) may be generated, which may cause the ultrasound therapy device to shut down or may generate a warning. If the actual profiles are sufficiently close to the stored profiles, then operation may continue (714), or a second signal may be produced, permitting operation of the ultrasound therapy device.

20 Claims, 7 Drawing Sheets

(51) Int. Cl.
    *A61B 17/00*    (2006.01)
    *A61N 7/00*    (2006.01)

(56)      References Cited

U.S. PATENT DOCUMENTS

| | | | | |
|---|---|---|---|---|
| 4,708,127 | A | * | 11/1987 | Abdelghani ...................... 601/2 |
| 4,984,449 | A | * | 1/1991 | Caldwell et al. ............... 73/49.2 |
| 5,517,994 | A | | 5/1996 | Burke et al. |
| 6,040,765 | A | | 3/2000 | Cherry et al. |
| 6,325,769 | B1 | | 12/2001 | Klopotek |
| 6,543,272 | B1 | * | 4/2003 | Vitek ............................ 73/1.83 |
| 7,675,430 | B2 | * | 3/2010 | Warner ........................ 340/12.5 |
| 8,282,554 | B2 | | 10/2012 | Makin et al. |
| 2004/0226378 | A1 | | 11/2004 | Oda et al. |
| 2005/0018453 | A1 | * | 1/2005 | Wofford .......................... 363/41 |
| 2005/0054926 | A1 | * | 3/2005 | Lincoln .......................... 600/443 |
| 2006/0122509 | A1 | | 6/2006 | Desilets |
| 2008/0051656 | A1 | | 2/2008 | Vaezy et al. |
| 2009/0036773 | A1 | * | 2/2009 | Lau ............................... 600/439 |
| 2009/0171252 | A1 | | 7/2009 | Bockenstedt et al. |

FOREIGN PATENT DOCUMENTS

| | | |
|---|---|---|
| EP | 0 871 019 A1 | 10/1998 |
| EP | 1 410 950 A2 | 4/2004 |
| JP | 61215982 | 9/1986 |
| JP | 08238243 | 9/1996 |
| JP | 2000060864 A | 2/2000 |
| JP | 2004025175 A | 1/2004 |
| JP | 06277223 A | 10/2006 |
| WO | WO 00/13598 A1 | 3/2000 |
| WO | WO 01/82806 A1 | 11/2001 |
| WO | WO 2004/110558 A1 | 12/2004 |
| WO | WO 2006/042163 A2 | 4/2006 |

OTHER PUBLICATIONS

European Patent Office, Written Opinion of the International Searching Authority issued in related International application No. PCT/US2010/028254 dated Sep. 23, 2011.

Japan Patent Office, Office Action issued in Japan Patent Application No. 2012-502159 dated Apr. 22, 2013.

* cited by examiner

ANALYSIS OF REAL TIME BACKSCATTER DATA FOR FAULT SIGNAL GENERATION IN A MEDICAL HIFU DEVICE

CROSS REFERENCE TO RELATED APPLICATION

This application claims the benefit of U.S. Provisional Application No. 61/162,641, filed on Mar. 23, 2009, the full disclosure of which is incorporated herein by reference.

BACKGROUND

Use of ultrasound to detect disturbances in a beam path is a well known application in medical devices. Various device manufacturers produce diagnostic ultrasound systems for imaging tissue, utilizing the basic principles of transmitting an ultrasound pulse into the body, then listening for the reflections. Reflections occur when the ultrasound beam crosses a barrier between different types of tissues, such as bone, muscle, fat or organs. Each boundary between a tissue type with different acoustic impedances produces a well known and well characterized type of reflection that allows diagnostic systems to identify objects in the beam path.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In an embodiment, there is a high intensity focused ultrasound therapy system with a method for detecting a system fault. The method involves transmitting a burst of ultrasonic energy from a high intensity focused ultrasound transducer mounted in a therapy head, capturing a ring down waveform after the burst, comparing the ring down waveform to an expected ring down waveform profile and generating a fault signal if the ring down waveform does not substantially match the expected ring down waveform profile.

The method may further include storing one or more expected ring down waveform profile(s) on a persistent memory device. The method may also involve preventing a high intensity focused ultrasound therapy system from operating after the fault signal is generated.

In an embodiment, there is a high intensity focused ultrasound therapy system having a method for detecting a system fault. The method involves transmitting a burst of ultrasonic energy from a high intensity focused ultrasound transducer mounted in a therapy head, applying a clamp impedance across the transducer, comparing the residual electrical voltage (clamp waveform) against a stored clamp waveform profile and generating a fault signal if the clamp waveform does not substantially match the stored clamp waveform profile.

In another embodiment, there is a method of determining functionality of an ultrasound therapy head. The method involves transmitting a burst of ultrasonic energy via a transducer that is mounted in a liquid filled therapy head, receiving one or more reflections from objects within the therapy head, the reflections comprising at least one waveform profile, comparing said waveform profile to an expected waveform profile for the therapy head, and generating a fault signal if the waveform profile of the reflection does not meet the expected waveform profile.

In various aspects of the embodiments, the expected waveform profile may have an expected amplitude range at a particular range of delays from the burst. Alternatively the expected waveform profile may have an expected maximum amplitude during an expected range of time after the burst. The expected waveform profile may have a permitted deviation from a set of defined amplitudes, each defined amplitude being a different delay from the burst. The method may involve generating a second signal if the actual waveform profile of the reflection does meet the expected waveform profile.

In other aspects of the embodiments, two or more reflections may be arranged in sequence and compared to a corresponding sequence of expected waveform profiles, the arrangement of reflections and expected waveforms being a linear time sequence. These expected waveform profiles may be a permitted deviation from a group of defined amplitudes, each defined amplitude being a different delay from the burst. The expected waveform profile may have a group of expected amplitude ranges, each expected amplitude range at a different delay from the burst. The expected waveform profile may have a group of expected maximum amplitudes, each expected maximum amplitude at a different expected range of time after the burst.

In another embodiment, there is a medical ultrasound therapy system. The system including a therapy head, a high intensity ultrasound transducer mounted in the therapy head, a data store storing information about expected waveform profiles of reflections of the transducer, and a controller linked to the data store and the transducer and operative to compare actual waveform profiles to the stored expected waveform profiles and to generate a first signal if the profiles do not substantially match. The controller may also operate to generate a second signal if the profiles do substantially match. The second signal may enable a treatment operation by the transducer. The first signal may disable a treatment operation by the transducer.

For a fuller understanding of the nature and advantages of the present invention, reference should be made to the ensuing detailed description and accompanying drawings.

DETAILED DESCRIPTION

Figure 1:
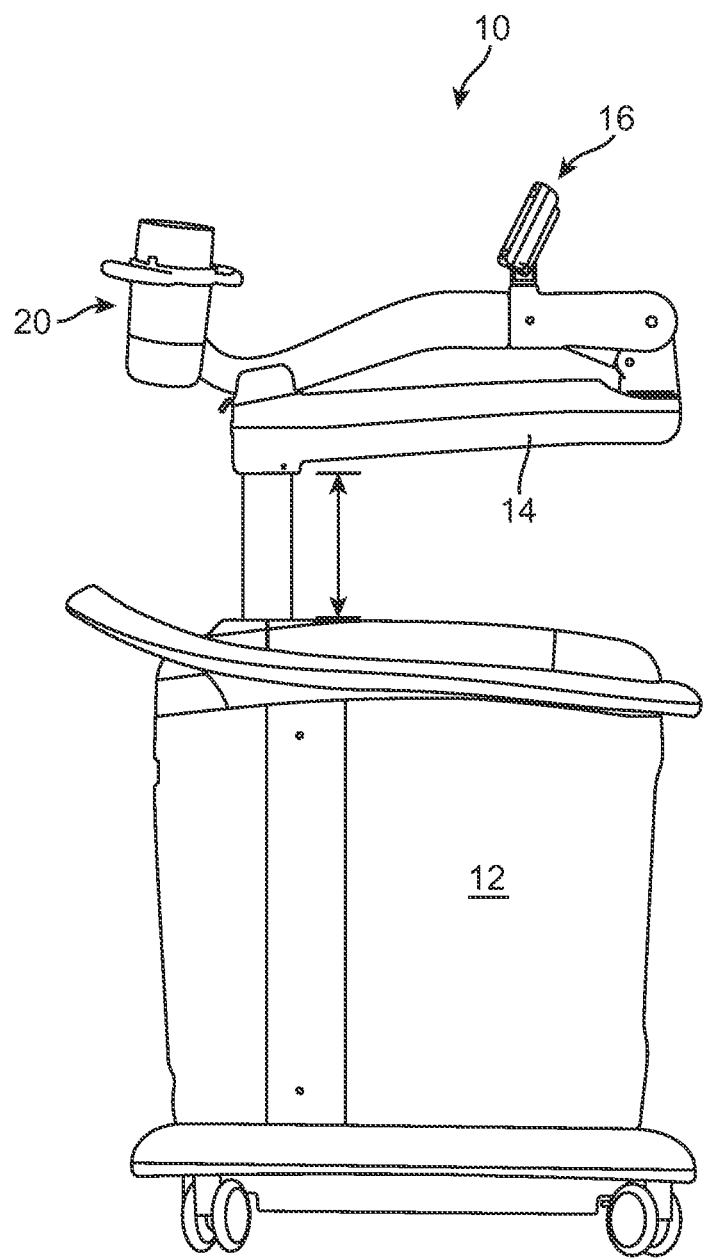
FIG. 1 shows an embodiment of a medical ultrasound system into which embodiments may be incorporated.

In the following paragraphs, various aspects and embodiments of the method and apparatus will be described. Specific details will be set forth in order to provide a thorough understanding of the described embodiments of the present invention. However, it will be apparent to those skilled in the art that the described embodiments may be practiced with only some or all of the described aspects, and with or without some of the specific details. In some instances, descriptions of well-known features may be omitted or simplified so as not to obscure the various aspects and embodiments of the present invention.

Parts of the description will be presented using terminology commonly employed by those skilled in the art to convey the substance of their work to others skilled in the art. The term system includes general purpose as well as special purpose arrangements of these components that are standalone, adjunct or embedded.

Various operations will be described as multiple discrete steps performed in turn in a manner that is most helpful in understanding the present invention. However, the order of description should not be construed as to imply that these operations are necessarily performed in the order they are presented, or even order dependent.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Described herein are various embodiments of a therapy head for use with a medical system. More particularly, therapy heads and related medical systems are provided that include an ultrasound transducer and a therapy processing module containing a processor, data store and controller that checks operation of the therapy head and generates a signal if the therapy head does not meet particular parameters. In an embodiment, as further described below, these parameters are based upon expected backscatter data received by the ultrasound transducer or electrical ring down of the transducer after the applied electrical stimulus.

In an embodiment, a high intensity focused ultrasound (HIFU) transducer is excited to generate a burst of ultrasound. As the ultrasound burst propagates from the transducer, various reflections are expected as the ultrasound wave encounters materials with different acoustic impedances in the beam path. These reflections are detected by the transducer and converted into an electrical signal in a reverse form of exciting the transducer. The measurement and analysis performed on these reflections vary by the signal processing algorithms of the various embodiments of the present invention. The reflections, echoes or other scattering of the acoustic wave following the pulse or burst transmission is collectively termed the "backscatter." Backscatter can be used to measure the strength of the reflection or echo, and the location of the object that caused the backscatter by using time of flight and the speed of sound in the medium to determine the distance from the transducer from the pulse.

The systems and methods of the various embodiments described herein may detect and compare the backscatter from one source, or multiple sources arranged in a variety of different formats, but generally the different reflections from a single ultrasound burst are measured in a linear time format. The systems and methods may analyze back scatter (reflections) from the ultrasound burst or "ring down" of the transducer after a burst. The electro-mechanical transient of the transducer after the application of an electrical drive burst or pulse is referred to herein as the transducer "ring down." By analogy, one might envision a bell. When the bell is struck, it issues forth sound. This is equivalent to the pulse or burst in the transducer. After being struck, a bell may still vibrate at a low level. This vibration is the mechanical energy bouncing around in the bell which eventually dissipates. The ring down of a transducer can be thought of as an analogy to the residual vibration in the bell. It is electro-mechanical energy after the pulse that dissipates over time and approaches zero. The time period required for the ring down to dissipate to a desired level is the ring down duration. The time interval during which the system looks at or measures the ring down signal is the ring down period. The ring down period may be arbitrarily defined and may be longer, shorter or the same time duration as the actual ring down duration.

In various embodiments of the systems and methods described herein, the burst or pulse of the transducer may be followed by an electrical clamp time. The clamp helps accelerate the dampening of the vibration of the transducer after a burst or pulse. The clamp provides an impedance across the transducer to increase the dissipation of any residual energy and hence reduce the ring down amplitude and duration of the transducer. Borrowing again from the bell analogy, the clamp down can be envisioned like a person placing their hand on the bell after it is struck to dampen the vibration. Certain types of defects in the transducer can cause the ring down duration and amplitude to increase. In this case the clamp time will not dissipate all the energy and the voltage after the clamp is removed will be much higher than normal. This excessive ring down voltage can be detected and used to indicate a defective transducer.

In addition to, or instead of, detecting and measuring the ring down of a transducer, the methods and systems of the various aspects of the invention may also monitor the clamp down time. During this time low waveform profile is expected due to the impedance placed across the transducer. If a different profile is observed then the clamp circuit may be damaged or the transducer characteristics may have changed dramatically.

In addition to, or instead of, detecting and measuring the ring down of a transducer, the methods and systems of the various aspects of the invention may also monitor for reflections within the treatment head (from objects in the coupling fluid or medium that are in the beam path, such as gas bubbles or particulate matter or large past reflections from the cap interface) and reflections from the cap of the treatment head (the boundary of the treatment head and patient). Reflections recorded for the latter reflections should generate an identifiable wave form for comparison. This waveform may be examined for both a minimum waveform pattern as well as a maximum waveform pattern. The minimum would check for the presence and location of the cap interface. The maximum pattern detection would check for proper coupling between the patient and the treatment head that would allow most of the energy to be coupled into the patient and not reflected back to the transducer. The former reflections should not produce significant waveforms during the interval where the ultrasound beam is in transit from the transducer to the cap. If a waveform is detected in this interval, the methods and systems of the various embodiments may produce a fault signal. Similarly, if the expected waveform of the cap reflection produces a waveform that is outside the acceptable waveform profiles, the systems and methods described herein may also generate a fault signal. A fault signal generated from any one of these monitored events will cause the system to cease operation. The detection of a fault event, and production of a fault signal, are intended as a safety feature for the HIFU system. The fault signal may be generated in response to any one of, or any combination of the detection events.

In another embodiment, a fault signal may be generated because there is no significant reflection from the cap, which may indicate the transducer or system itself failed to pulse. Such a failure mode may be detected by setting the expected reflection amplitude as a minimum threshold, below which a fault is generated.

In the various embodiments described herein, the safety of the patient and efficacy of the treatment are the primary concern. If the systems and methods as described herein operate without detecting the various faults, a patient may suffer skin burns during treatment, or the expected energy dose delivered to the patient may be reduced substantially. Further the device itself may generate sufficient reflected energy to the transducer, or internal cavitation may occur, such as to destroy or seriously damage the transducer and other components within the transducer chamber. The detection of any faults as described herein are referred to as system faults, whether they originate in the transducer, therapy head or other component that results in fault signal produced by the methods and/or systems described herein.

Discussion herein of the waveform profile generally refers to the various parameters that are capable of being measured by the system and methods described herein. These parameters may include any one or more of the following: the amplitude of the reflection, the frequency of the reflection signal, the duration of the reflection, the time delay of the reflection as measured from time after the initial burst, or the delay after any one of the other parameters described herein, the general shape of the reflection envelope (e.g. a square wave, a ramp wave, etc. ... ) Similar parameters (amplitude, frequency, duration, time delay, and shape) may also apply to the ring down or clamp time.

Referring now to the drawings, in which like reference numerals represent like parts throughout the several views, FIG. 1 shows a medical ultrasound system 10 that may be used with embodiments of the invention. The medical ultrasound system 10 may include a base unit 12, an articulating arm 14 attached to the base unit, and a user interface device 16 attached to the articulating arm 14. At the distal end of the articulating arm 14 is an ultrasound therapy head 20.

Figure 2:
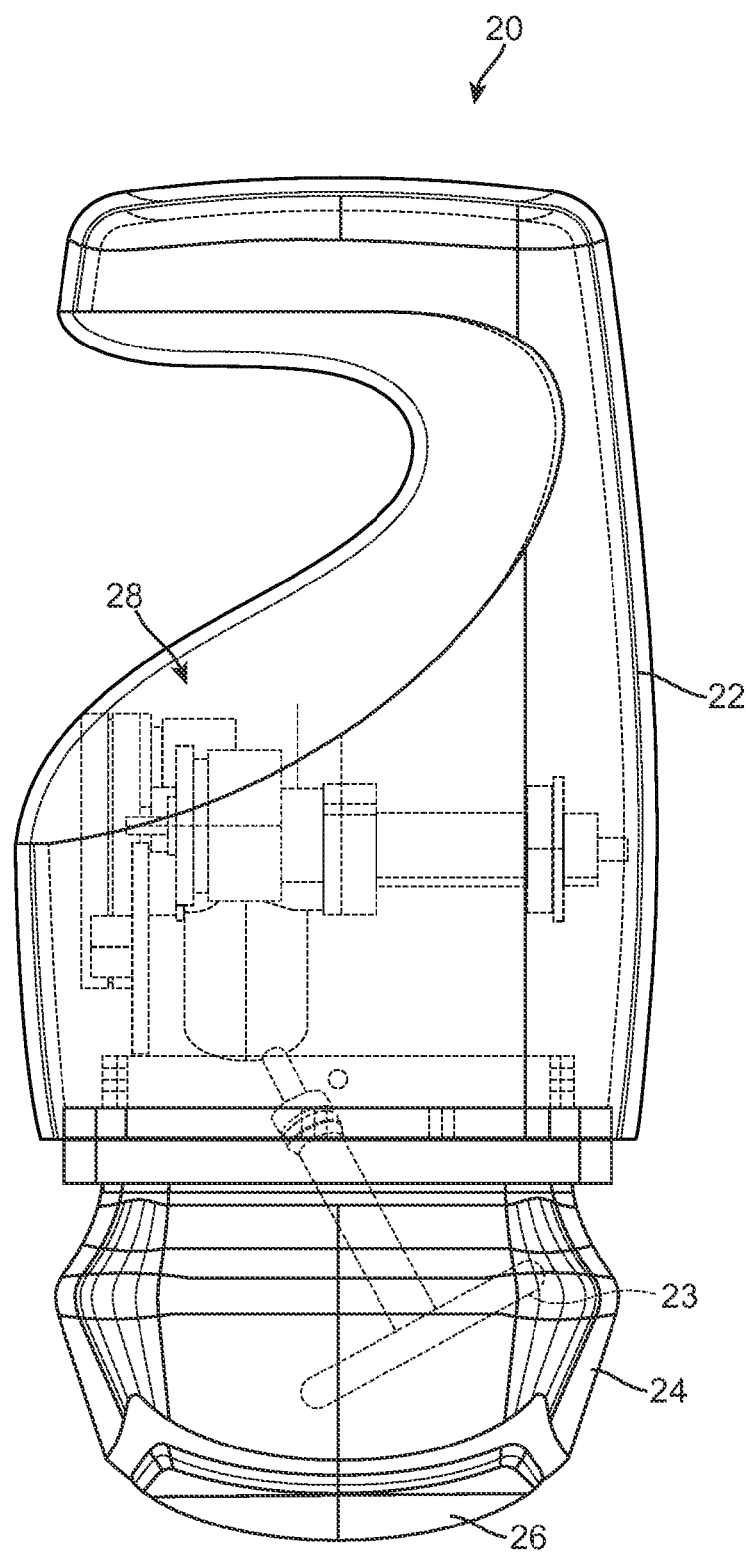
FIG. 2 shows a therapy head for the medical ultrasound system of FIG. 1.

The exterior of the ultrasound therapy head 20 may be a form factor that is easily handled by an operator. An example of one embodiment is shown in FIG. 2, but the ultrasound therapy head may take many other forms. The ultrasound therapy head 20 may have cables extending from it and going to the base unit 12 through the articulating arm 14, or the cables may optionally be exposed.

As shown in FIG. 2, the ultrasound therapy head 20 includes an upper compartment 22, and a lower compartment 24, or ultrasound chamber. The ultrasound chamber has a cap. The upper compartment 22 may be dry and house wires, cables, a motor assembly, and/or other features for a transducer 23, which may be mounted in the lower compartment 24. The lower compartment 24 preferably contains a coupling fluid, such as water, or other medium, used to transfer ultrasound energy from the transducer 23 to and through a window 26 located near the bottom of the lower compartment. Other fluids, gels or solid materials may also be used as the coupling medium. Disposed within the upper compartment 22 is an actuation assembly 28. The actuation assembly 28 provides for control over the position/orientation of the transducer 23 located within the lower compartment 24. An example of an actuation assembly is described in U.S. patent application Ser. No. 12/364,327, filed Feb. 2, 2009, and entitled "Therapy Head for Use with an Ultrasound System."

In operation, a technician rolls the medical ultrasound system 10 to adjacent a patient. The technician grasps and moves the ultrasound head 20, with the ultrasound head 20 remaining attached to the articulating arm 14. The ultrasound head 20 may be aligned so that the window 26 is in contact with the patient. The user interface device 16 may be operated to generate an appropriate treatment or diagnostic test. During use, the transducer mounted in the lower compartment 24 generates ultrasound energy, which may be used, for example, for the destruction of adipose tissue, as described in U.S. Published Application No. 2006/0122509. The actuation assembly 28 can be used to provide for simplified treatment procedures. For example, the ultrasound head 20 can be held in stationary contact with the patient while the actuation assembly 28 varies the position/orientation of the ultrasound transducer so as to apply therapeutic treatment to a local region of the patient using a scan pattern that provides a desired coverage, duration, spacing, etc.

Figure 3:
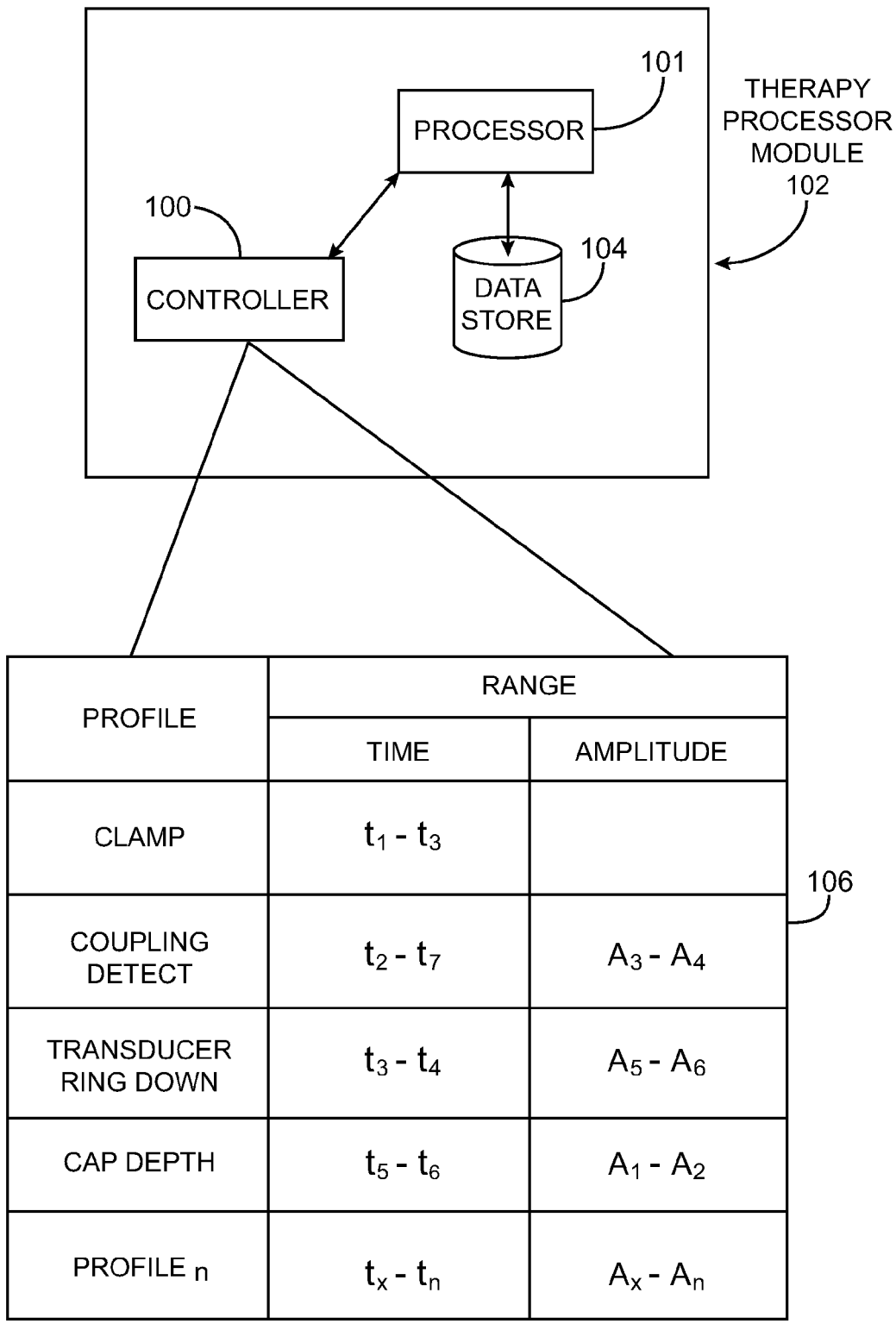
FIG. 3 is a block diagram showing components of a controller for the medical ultrasound system of FIG. 1 in accordance with an embodiment.

FIG. 3 shows a Therapy Processor Module 102 that may be used in the medical ultrasound system 10. The Therapy Processor includes a processor 101 and a controller 100. The processor 101 may be a standard control (i.e., a device or mechanism used to regulate or guide the operation of a machine, apparatus, or system), a microcomputer, or any other device that can execute computer-executable instructions, such as program modules. Generally, program modules include routines, programs, objects, components, data structures and the like that perform particular tasks or implement particular abstract data types.

The processor 101 sets up the operation of controller 100 using execution instruction stored in a persistent memory device in conjunction with any data input from an operator. Such data can, for example, be input through a user interface, such as the graphical user interface 16. Thus, processor 101 can include an execution area into which execution instructions are loaded from memory. These execution instructions will then cause processor 101 to send commands to controller 100, which provides the real time control for the operation of transducer 23 and/or other portions of the system 10.

The therapy processing module 102 may also include, or is otherwise associated with, a data store 104. The data store 104 stores information in the form of one or more data tables, with one table 106 illustrated. The profiles shown correspond to the events that should produce an expected echo or reflection. Addition profiles $PROFILE_n$ with desired time and amplitude ranges may be defined if desired, based on any additional reflections the system and/or methods may want to compare against established profile data.

Figure 4:
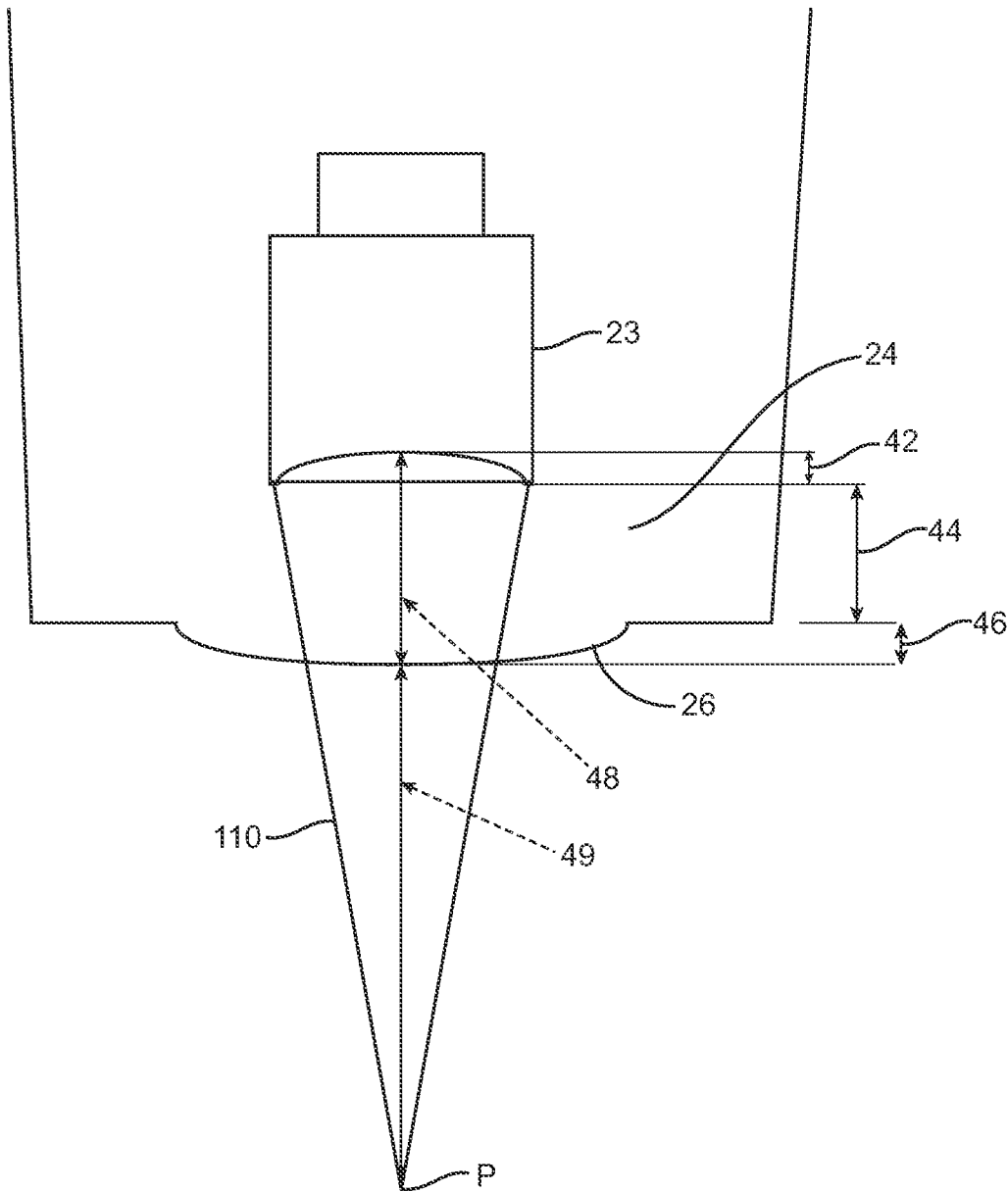
FIG. 4 shows a diagrammatic representation of transmission and reflections of ultrasound generated and received by a transducer in accordance with an embodiment.

FIG. 4 shows a diagrammatic representation of transmission of ultrasound by the transducer 23 in accordance with an embodiment. As stated above, the transducer 23 is mounted in the lower housing 24, which in an embodiment is filled with a coupling fluid, such as degassed water. The outer portion of the lower housing 24 is covered with the transmissible window 26, which may be, for example, Kapton. The window is substantially transparent to ultrasound energy. The transducer 23 may be mechanically focused or an array and have a depth variation 42 measured from the transducer center to the face or lip of the transducer edge. If the transducer is a flat array, the depth variation will be zero. The transducer has a nominal height 44 within the lower housing, and the transducer may be moved up or down with respect to the window 26. The nominal height 44 may vary by centimeters or fractions of a millimeter depending on the application the treatment head may be designed for. The cap height 46 is the difference in depth from the plane of the cap closest to the transducer, to the most extended position of the cap. The cap may be placed against a person's skin during operation of the transducer. The cap may be flexible and capable of variable expansion, requiring adjustment in calculation depending on the cap height. The nominal height of the transducer 44 plus the cap height 46, plus any depth variation in the transducer, produces the cap depth 48. The treatment depth 49 is the distance from the outside edge of the cap to the focal zone of the transducer. Generally the data table contains all the required height adjustment information of the transducer center to face measurement 42, nominal transducer height measurement 44, cap height 46, cap depth 48 and overall treatment depth 49.

In general, the transducer 23 may be shaped for mechanical focusing, or include an array so that ultrasonic pulses may form a beam 110 that converges at a focal point P. In use, the focal point P is within a patient's body. In traveling to the focal point P, the ultrasound beam 110 travels through medium in the transducer chamber in the lower compartment 24, through the transmissible window 26, through a interface with the patient's body, which may be any suitable ultrasound coupling agent, such as water or very light solutions composed mainly of water. The beam then travels to the focal point P in the patient's body.

Air pockets within the treatment head, or an improper coupling of the window 26 with a patient, and other irregularities may decrease the energy provided by the beam 110 to the focal point P. Gas bubbles or obstructions within the transducer chamber may obstruct or interfere with the beam path. Any reflections from gas bubbles or other obstructions in the beam path inside the transducer chamber will produce an unexpected return waveform as the ultrasound propagates through the region 48. If the window 26 is improperly coupled to the patient, the coupling detect 526 (FIG. 5A) may produce a larger than expected waveform, and also trigger a fault signal.

Such irregularities generally produce reflections of the ultrasound energy beam 110. Moreover, reflections occur in the lower compartment or at its juncture with the patient, for example at the window 26, which should be coupled to the patient. In accordance with an embodiment, the controller 100 compares such reflections to stored expected values for reflections maintained in the data store 104. If such reflections do not meet a value or range of values stored in the data store 104, then a fault signal may be generated, for example to provide a warning or to shut down the transducer 23. Alternatively, a detected wave from where none are expected may also produce a fault signal. The region 48 between the transducer to the near edge of the cap 48, is the region where little reflection is expected. A significant return in that interval could indicate an obstruction or lack of coupling and may generate a fault signal.

In an embodiment, the values stored in the data store 104 represent a profile of an expected reflection. The profile may be affected by the many parameters described herein. Some flexibility may be built in to the system memory, data library or comparison algorithm, to compensate for nominal variations in performance, environment and/or user capabilities. The particular shape may be expected at a particular delay from transmission.

A comparison may be used for checking functionality of the ultrasound therapy head. In the comparison, the waveform profile for ultrasound reflections for a functional therapy head are stored, and before use of a therapy head, an ultrasound energy burst is sent, and the actual waveform profile of the returned reflections are compared to the stored waveform profiles. If the actual profiles are not sufficiently close to the stored profiles, then a first signal may be generated, which may cause the ultrasound therapy device to shut down, pause, or may generate a warning. If the actual profiles are sufficiently close to the stored profiles, then operation may continue, or a second signal may be produced, the second signal permitting operation of the ultrasound therapy device. The sample signal may be the same as the therapy signal, be broadcast at regular intervals and/or incorporated into the therapy pulses driven to the transducer. Alternatively the some embodiments may use the first pulse (or any identified pulse) in a series of pulses to perform the fault check. The pulse may be low power or normal therapy power and may be used for therapy or only for generating the sample signal, so long as the system algorithms, data library and/or processor compensate for the differences in the pulse used for detecting faults. Alternatively a delay time may be inserted in the pulses to allow reflections from previous bursts to dissipate to allow for a more sensitive measure of low level reflections on the next pulse. Note that the different algorithms that operate on the waveforms may operate at independent rates and sample the data returned from different pulses.

Figure 5A:
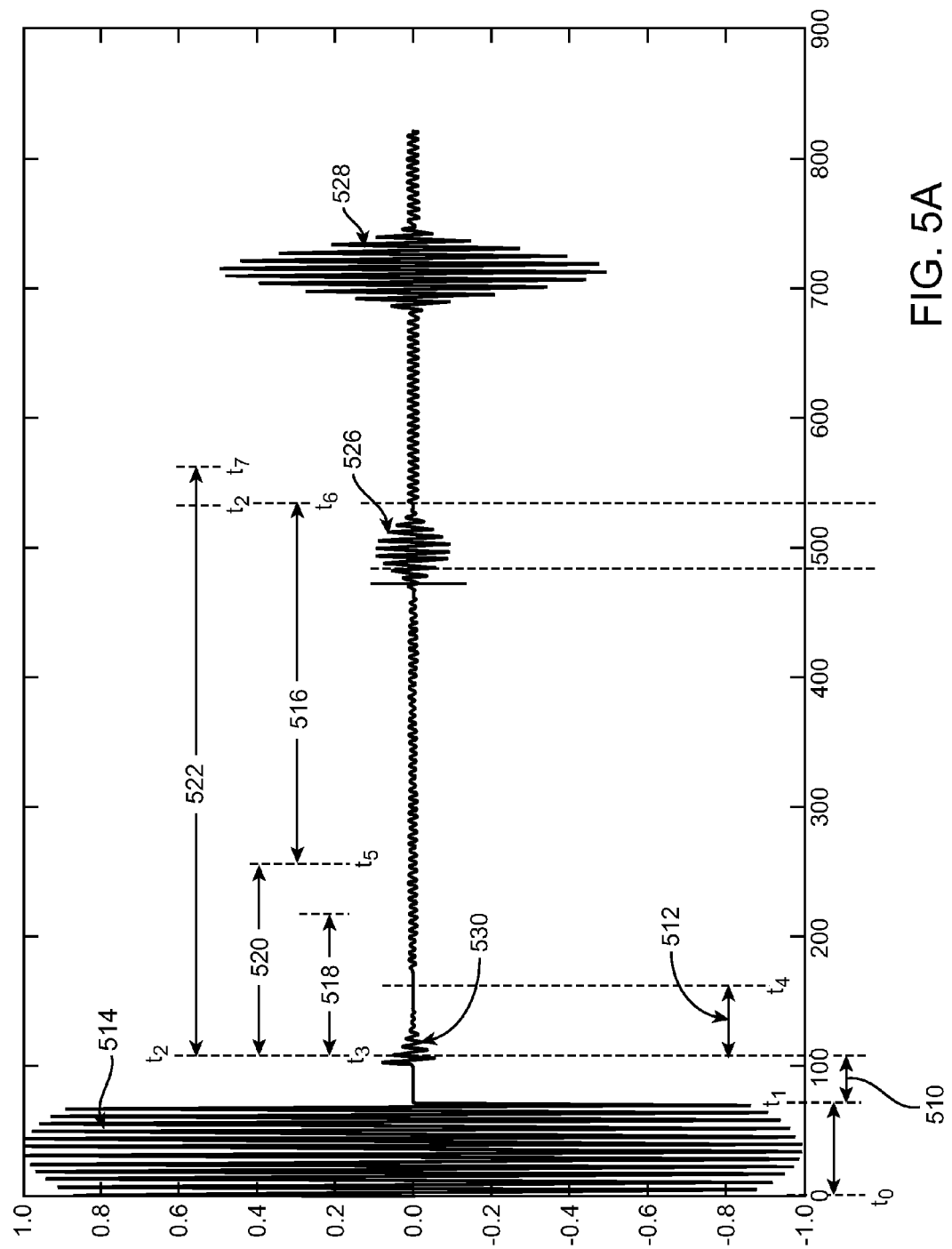
FIG. 5A shows a linear sequence of possible expected waveforms following a pulse.

Examples of some expected waveforms are provided in a time based linear sequence (FIG. 5A). The graph provides the wave amplitude on the Y axis and the time delay on the X axis. The initial pulse starts at coordinate 0,0 on the graph, or $t_o$. The initial pulse or burst is shown as 514. Following the initial pulse 514 is the clamp duration 510 ($t_1$-$t_3$). When the clamp duration ends, the residual vibration in the transducer can be measured as the ring down. Due to the nature of the clamp, it has low amplitude, which may or may not be measured. The transducer ring down time interval 512 ($t_3$-$t_4$) is the period where a ring down check occurs. There is a calculated cap detection period 520 for running the cap detection algorithm. The cap detection period location is determined based on the transducer position relative to the cap. A coupling check period 522 is used for running the couple detect algorithm. The coupling detect time interval is shown between $t_2$-$t_7$. The cap check time 516 (referred to as the cap depth in FIG. 3, $t_5$-$t_6$) is used to look for the cap waveform profile to measure the cap location to verify the treatment head cap is operating properly and that the treatment depth will be at the correct location. The coupling detect period 522 ($t_2$-$t_7$) is used to determine if any obstructions are in the acoustic path and to verify that the treatment head cap is properly coupled to the patient. On the right end of the acoustic wave pattern is the focus backscatter 528, which is ignored for the purposes of the methods and systems of the various embodiments of the invention. Additional profiles (PROFILE$_n$) may be defined if desired, each having a time delay from burst ($t_x$-$t_n$) and amplitude ($A_x$-$A_n$). Within each period of detection, the system may have a built in amount of variability to prevent false positives from generating fault signals. Typically the system has a built in tolerance for both differences in the delay times from burst (or delay time from another measured parameter), amplitude, frequency and other parameters used to measure the wave forms to allow the system to operate without generating false fault signals. These tolerances are permitted deviations from the expected waveforms.

Figure 5B:
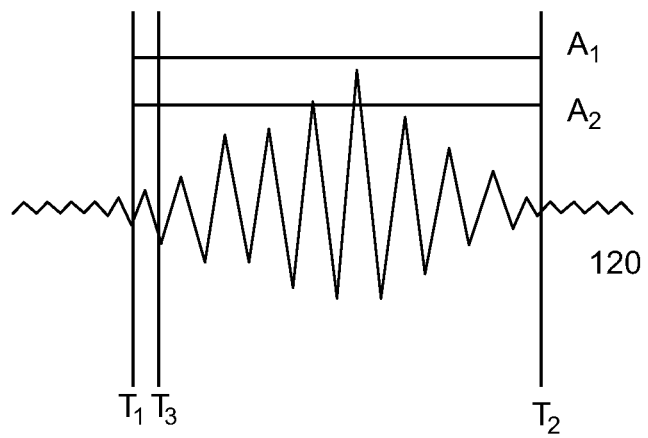
FIG. 5B shows evaluation of a waveform with respect to an expected profile in accordance with an embodiment.

The shape of the waveform profile may have two ranges of boundaries, for example within a time range between $t_1$ and $t_2$, and having a amplitude between $A_1$ and $A_2$. In this embodiment, a waveform 120 (FIG. 5B) between times $t_1$ and $t_2$ includes a maximum amplitude between $A_1$ and $A_2$, then the waveform meets the criteria set by the therapy processing module 102. If the maximum amplitude of the waveform profile extends outside of the boundaries of the acceptable amplitude between A1 and A2, it does not meet the expected profile, and a fault signal may be generated. The waveform shown in FIG. 5B is merely illustrative. The waveform profiles stored in memory may be any shape. Comparison ranges may be designated to match the many parameters described herein.

For the example in FIG. 5B, the controller module 100 may evaluate whether the start of a reflection begins between $t_1$ and some other time, such as $t_3$. Such a determination may involve an evaluation of whether the amplitude for the waveform meets a particular threshold at this level. Similarly, an evaluation may be made regarding the end of the waveform.

Figure 6:
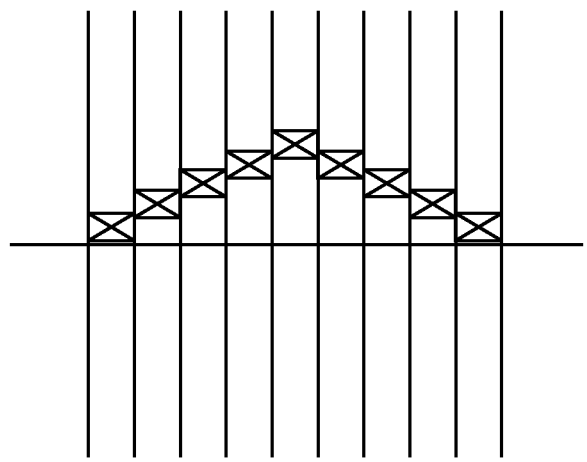
FIG. 6 shows evaluation of a waveform with respect to an expected profile in accordance with another embodiment.

As an alternative, a more defined waveform may be stored in the data store 104, broken into a series of time segments having expected ranges of amplitudes and frequencies. Thus, as shown in FIG. 6, for each time segment, there is an expected amplitude range (including an "X" in each range shown in FIG. 6), represented an acceptable amplitude range at that time segment for certain frequencies of signals.

As another alternative, a defined waveform pattern may be stored in the data store, with lines defined for expected amplitudes at a given times, and variations by a defined amount (plus or minus 5%, for example), may result in a signal.

As yet another alternative, the profile may be an integration of the expected amplitude over a time period, and the integration of a measured amplitude over a defined time interval may be compared to this expected profile.

As yet another alternative, the controller may use a correlation or cross correlation algorithm over a defined time interval of the profile and the measured signal.

A number of alternatives are available, but in general, the therapy processing module 102 evaluates the profile of the waveform verses an expected profile.

Figure 7:
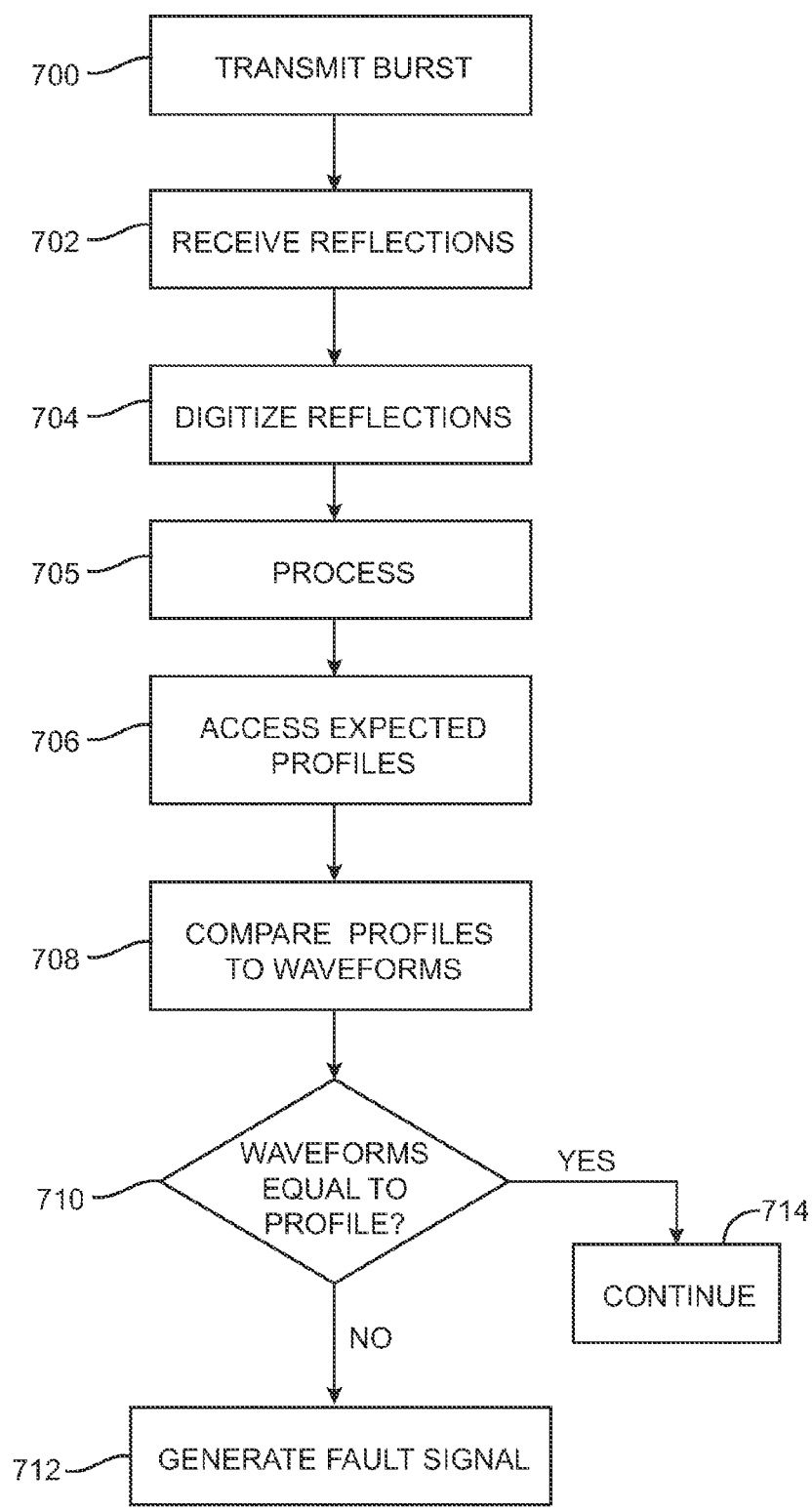
FIG. 7 is a flow chart representing a method for comparing a waveform to an expected profile in accordance with an embodiment.

FIG. 7 is a flow chart representing a method for comparing a waveform to an expected profile in accordance with an embodiment. Beginning at step 700, a burst is transmitted from the transducer 23. At step 702, reflections from the burst are received, most likely at the transducer. The reflections are digitized at step 704. The signal may be filtered in the analog domain before the digitization step 704. The digitized reflections are the processed through the various algorithms in 705 to prepare the digitized received signals to be compared to the expected profiles.

At step 706, the expected profile for waveforms of the reflections are accessed. For example, as shown in FIG. 3, the table 106 may have stored therein a number of different expected profiles. In the embodiment shown in the drawings, these profiles represent cap depth (distance from window 26 to transducer 23), coupling detect (coupling with patient), and transducer ring down (excessive electrical ringing of the transducer after a transmit burst is complete), although other features may be detected.

At step 708, the waveforms are compared to the profiles. If a waveform does not meet a profile, then step 710 branches to step 712, where a fault signal is generated. This signal may be, for example, a warning, or a fault signal forcing pause or shut down of the transducer 23 or the system 10. If the waveforms do meet the profiles, the operation is continued at step 714. This step may include, for example, generating a second signal indicating operation is available, or allowing operation. It should be noted that the profile may also be defined so that if the profile is met it is considered a fault condition and can generate a fault.

Additional alternative embodiments of the present invention will be readily apparent to those skilled in the art upon review of the present disclosure. The lack of description or the embodiments described herein should not be considered as the sole or only method and apparatus of providing for use of real time backscatter data to determine the correct operation, placement and use of a HIFU device. The scope of the present invention should not be taken as limited by the present disclosure except as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for detecting a transducer fault in a high intensity focused ultrasound therapy system, the method comprising:

transmitting a burst of ultrasonic energy or a pulse of ultrasonic energy from a high intensity focused ultrasound transducer mounted in a therapy head;

after the burst of ultrasonic energy or the pulse of ultrasonic energy is transmitted, applying an electrical clamp to the transducer that provides an impedance across the transducer and accelerates vibration dampening of the transducer after the burst of ultrasonic energy or the pulse of ultrasonic energy;

after the application of the electrical clamp ends, measuring a clamp waveform comprising residual electrical voltage;

comparing the clamp waveform against a stored clamp waveform profile; and if the clamp waveform does not substantially match the stored clamp waveform profile, generating a fault signal.

2. The method of claim 1, wherein the expected clamp waveform profile is stored on a persistent memory device.

3. The method of claim 1, further comprising:
preventing the high intensity focused ultrasound therapy system from operating after the fault signal is generated.

4. A method of determining functionality of a medical ultrasound therapy head, the method comprising:
while a cap of the medical ultrasound therapy head is in contact with the patient, transmitting a burst of ultrasonic energy via a transducer that is mounted in the medical ultrasound therapy head;
receiving one or more reflections of the ultrasonic energy in the burst from objects other than the transducer within the medical ultrasound therapy head, the reflections comprising at least one waveform profile;
comparing the at least one waveform profile to an expected waveform profile for the therapy head;
generating a first signal indicating a fault if the waveform profile does not match the expected waveform profile; and
preventing an ultrasound therapy system from operating after the first signal is generated.

5. The method of claim 4, wherein the expected waveform profile comprises an expected amplitude range at a particular range of delays from the burst.

6. The method of claim 4, wherein the expected waveform profile comprises an expected maximum amplitude during an expected range of time after the burst.

7. The method of claim 4, wherein the expected waveform profile comprises an expected minimum amplitude during an expected range of time after the burst.

8. The method of claim 4, wherein the expected waveform profile comprises a permitted deviation from a plurality of defined amplitudes, each defined amplitude being a different delay from the burst.

9. The method of claim 4, further comprising:
generating a second signal indicating operation is available if the actual waveform profile of the reflection does meet the expected waveform profile.

10. The method of claim 4, wherein a plurality of reflections are arranged in sequence and compared to a corresponding sequence of expected waveform profiles, the arrangement of reflections and expected waveforms being a linear time sequence.

11. The method of claim 10, wherein the expected waveform profile comprises a permitted deviation from a plurality of defined amplitudes, each defined amplitude being a different delay from the burst.

12. The method of claim 10, wherein the expected waveform profile comprises a plurality of expected amplitude ranges, each expected amplitude range at a different delay from the burst.

13. The method of claim 10, wherein the expected waveform profile comprises a plurality of expected maximum amplitudes, each expected maximum amplitude at a different expected range of time after the burst.

14. The method of claim 4, further comprising:
capturing a ring down waveform after the burst;
comparing the ring down waveform to an expected ring down waveform profile; and
if the ring down waveform does not substantially match the expected ring down waveform profile, generating another fault signal.

15. The method of claim 14, wherein one or more expected ring down waveform profiles are stored on a persistent memory device.

16. The method of claim 14, further comprising:
if the ring down waveform does not substantially match the expected ring down waveform profile, preventing the ultrasound therapy system from operating.

17. An ultrasound therapy system comprising:
a medical ultrasound therapy head including a transducer and a cap;
a processor; and
a program module configured upon execution by the processor to determine functionality of the medical ultrasound therapy head, wherein the program module is configured to the determine the functionality of the medical ultrasound therapy head by:
while the cap of the medical ultrasound therapy head is in contact with the patient, transmitting a burst of ultrasonic energy via the transducer;
receiving one or more reflections of the ultrasonic energy in the burst from objects other than the transducer within the medical ultrasound therapy head, the reflections comprising at least one waveform profile;
comparing the at least one waveform profile to an expected waveform profile for the therapy head;
generating a fault signal if the waveform profile of the reflection does not meet the expected waveform profile; and
preventing the ultrasound therapy system from operating after the fault signal is generated.

18. The ultrasound therapy system of claim 17, further comprising:
a persistent memory device configured to store one or more expected waveform profiles.

19. The ultrasound therapy system of claim 17, wherein the program module is configured to the determine a functionality of the transducer by:
capturing a ring down waveform after the burst;
comparing the ring down waveform to an expected ring down waveform profile; and
if the ring down waveform does not substantially match the expected ring down waveform profile, generating another fault signal.

20. The ultrasound therapy system of claim 19, wherein the program module is further configured to prevent the ultrasound therapy system from operating if the ring down waveform does not substantially match the expected ring down waveform profile.

* * * * *

UNITED STATES PATENT AND TRADEMARK OFFICE
CERTIFICATE OF CORRECTION

PATENT NO. : 9,816,968 B2  
APPLICATION NO. : 12/729447  
DATED : November 14, 2017  
INVENTOR(S) : Blake Little Page 1 of 1

It is certified that error appears in the above-identified patent and that said Letters Patent is hereby corrected as shown below:

In the Claims
Column 12, Claim 17, Line 32, after "configured to" delete "the"

Signed and Sealed this
Twentieth Day of February, 2018

Andrei Iancu
*Director of the United States Patent and Trademark Office*